US011650651B2

United States Patent
Coughlin et al.

(10) Patent No.: US 11,650,651 B2
(45) Date of Patent: *May 16, 2023

(54) DYNAMIC POWER REDUCTION TECHNIQUE FOR ULTRASOUND SYSTEMS

(71) Applicant: FUJIFILM SONOSITE, INC., Bothell, WA (US)

(72) Inventors: Justin M Coughlin, Bothell, WA (US); Mitchell S. Kaplan, Bothell, WA (US); Michael R. Hansen, Bothell, WA (US); William R. Ogle, Bothell, WA (US)

(73) Assignee: FUJIFILM SONOSITE, INC., Bothell, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/725,174

(22) Filed: Apr. 20, 2022

(65) Prior Publication Data
US 2022/0391006 A1 Dec. 8, 2022

Related U.S. Application Data

(63) Continuation of application No. 16/803,726, filed on Feb. 27, 2020, now Pat. No. 11,493,979.

(51) Int. Cl.
*G06F 1/3237* (2019.01)
*G01S 15/89* (2006.01)
(Continued)

(52) U.S. Cl.
CPC .......... *G06F 1/3237* (2013.01); *G01S 7/521* (2013.01); *G01S 7/526* (2013.01); *G01S 15/8906* (2013.01); *G06F 1/08* (2013.01)

(58) Field of Classification Search
CPC .......... G06F 1/3237; G06F 1/08; G01S 7/521; G01S 7/526; G01S 15/8906
See application file for complete search history.

(56) References Cited

U.S. PATENT DOCUMENTS 8,090,065 B2 * 1/2012 Gabrielson ........... H04L 7/0337
375/362
RE46,185 E * 10/2016 Mehi .................... A61B 8/565
(Continued)

FOREIGN PATENT DOCUMENTS

| WO | WO-2016127130 A1 * | 8/2016 | ........... A61B 5/0031 |
| WO | WO-2019145141 A1 * | 8/2019 | ........... A61B 8/0841 |
| WO | WO-2021173585 A1 * | 9/2021 | ......... G01S 15/8906 |

OTHER PUBLICATIONS

International Preliminary Report and Written Opinion on the Patentability of Application No. PCT/US2021/019287 dated Sep. 9, 2022, 7 pages.

*Primary Examiner* — Daniel Pihulic
(74) *Attorney, Agent, or Firm* — Womble Bond Dickinson (US) LLP (57) ABSTRACT

A dynamic power reduction method and apparatus for use in an ultrasound system are described. In one embodiment, the ultrasound system comprises: a transducer assembly and imaging subsystem having a transmit data path having a transmitter to transmit acoustic signals and a receive data path having including signal acquisition circuitry with a receiver to receive acoustic signals representing echoes; a plurality of real-time signals indicative of status of imaging operations being performed by the transmit and receive paths; a clock generator to generate one or more clocks for use by the transmit and receive data paths; clock gating circuitry coupled to the clock generator and the transmit and receive paths and having circuits to gate clocks to at least one of the transmit and receive paths; and a clock gating controller coupled to the clock gating circuitry to control the circuits to gate or pass clock signals to at least one of the transmit and receive paths automatically in response to receipt of one or more signals from the plurality of real-time signals.

20 Claims, 7 Drawing Sheets

(51) Int. Cl.
*G06F 1/08* (2006.01)
*G01S 7/521* (2006.01)
*G01S 7/526* (2006.01)

(56) References Cited

U.S. PATENT DOCUMENTS

| | | | |
|---|---|---|---|
| 2009/0105587 A1* | 4/2009 | Petersen | G01S 7/5208 600/437 |
| 2018/0248477 A1* | 8/2018 | Kline | H02M 1/08 |
| 2021/0271309 A1* | 9/2021 | Coughlin | G01S 7/52085 |

* cited by examiner

DYNAMIC POWER REDUCTION TECHNIQUE FOR ULTRASOUND SYSTEMS

RELATED APPLICATION

The present application is a continuation of and claims the benefit of U.S. patent application Ser. No. 16/803,726, filed on Feb. 27, 2020 and entitled "Dynamic Power Reduction Technique for Ultrasound Systems," and is incorporated herein by reference in its entirety.

FIELD OF THE INVENTION

Embodiments of the present invention relate generally to ultrasound systems; more particularly, embodiments of the present invention relate to performing power management in ultrasound systems based on real-time signals.

BACKGROUND

System power consumption in an ultrasound machine represents a significant problem for a designer. There are a number of adverse effects resulting from high system power consumption. Such ultrasound machines include larger, more expensive power supplies, have shorter battery lives, increased internal operating temperature, utilize active cooling components that add system cost, complexity and noise, and have an increased physical footprint.

Power consumption has been addressed at a macro level. More specifically, from a historical perspective, the power consumption problem in ultrasound machines has been addressed by defining sleep states for the machine that are generally under the control of the ultrasound machine's software. In the sleep state(s), portions of the system are put in a low power state (e.g., a lower power consumption state) by slowing or stopping the digital clock(s) controlling the block(s). The result is placing portions of the system in a lower power state is the reduction, and potentially minimization, of the dynamic power of the system. These states are generally defined at a macro level such that they do not occur when performing macro functions such as active imaging, and generally are applied when the ultrasound machine is idle.

Figure 1:
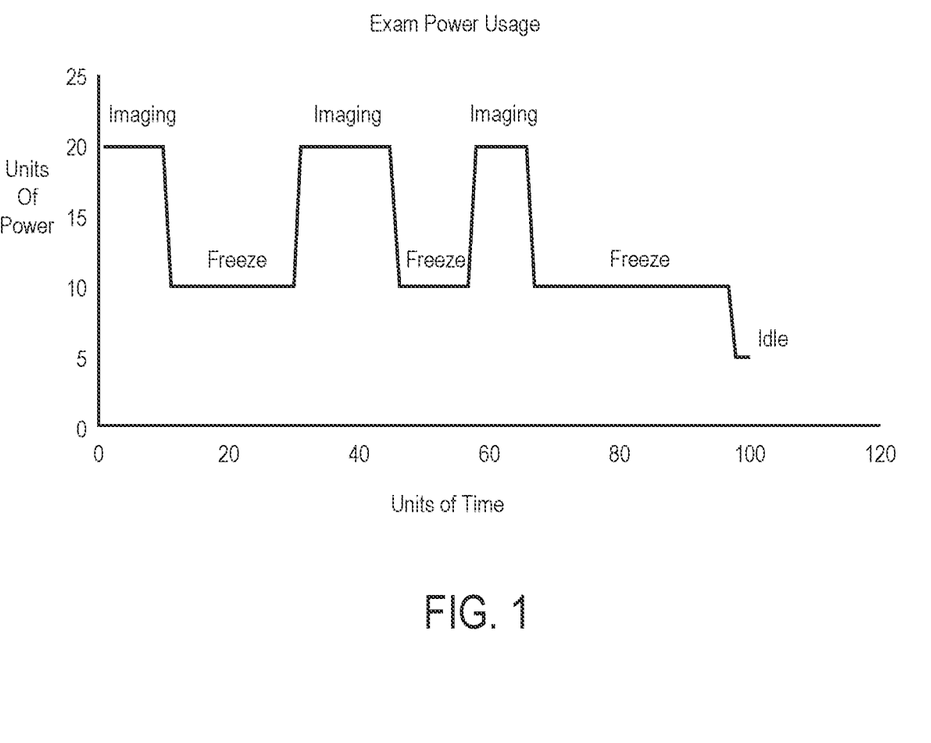
FIG. 1 illustrates power usage at a macro level during an ultrasound exam.

FIG. 1 illustrates power usage at a macro level during an ultrasound exam. In the Imaging state, data is acquired and displayed in real-time. At this time, the system power consumption is generally at a maximum as most of the electronics are active. When the user stops imaging and reviews the acquired data, the system software can shut down most of the electronics associated with data acquisition while leaving the display and image recall electronics running. This state of the ultrasound machine is often referred to as a Freeze state. During an exam, the user may toggle between Imaging and Freeze states multiple times. Finally, after a certain time duration in the Freeze state, the system software may shut down the display and enter an even lower power state depicted as Idle in FIG. 1.

To exploit the sleep state concept, the system software must be written to recognize opportunities to go to sleep and events requiring the system to wake up. The net effect is that the software design and verification are complicated to achieve power savings.

SUMMARY OF THE INVENTION

A dynamic power reduction method and apparatus for use in an ultrasound system are described. In one embodiment, the ultrasound system comprises: a transducer assembly and imaging subsystem having a transmit data path having a transmitter to transmit acoustic signals and a receive data path having including signal acquisition circuitry with a receiver to receive acoustic signals representing echoes; a plurality of real-time signals indicative of status of imaging operations being performed by the transmit and receive paths; a clock generator to generate one or more clocks for use by the transmit and receive data paths; clock gating circuitry coupled to the clock generator and the transmit and receive paths and having circuits to gate clocks to at least one of the transmit and receive paths; and a clock gating controller coupled to the clock gating circuitry to control the circuits to gate or pass clock signals to at least one of the transmit and receive paths automatically in response to receipt of one or more signals from the plurality of real-time signals.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

DETAILED DESCRIPTION

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

An ultrasound system having dynamic power reduction and method for using the same are disclosed. In one embodiment, the dynamic power reduction is performed using hardware of an acoustic signal path to automatically detect power saving and transparently control digital clocks without the intervention of the system software. In one embodiment, the hardware-based dynamic power reduction is performed in cooperation with or in addition to the macro sleep conditions discussed above. In one embodiment, the hardware-based dynamic power reduction is configured to reduce power while actively imaging. In one embodiment, the power reduction is equal to or greater than the software-controlled sleep techniques discussed above and have the added benefit of no additional software complexity.

Figure 2:
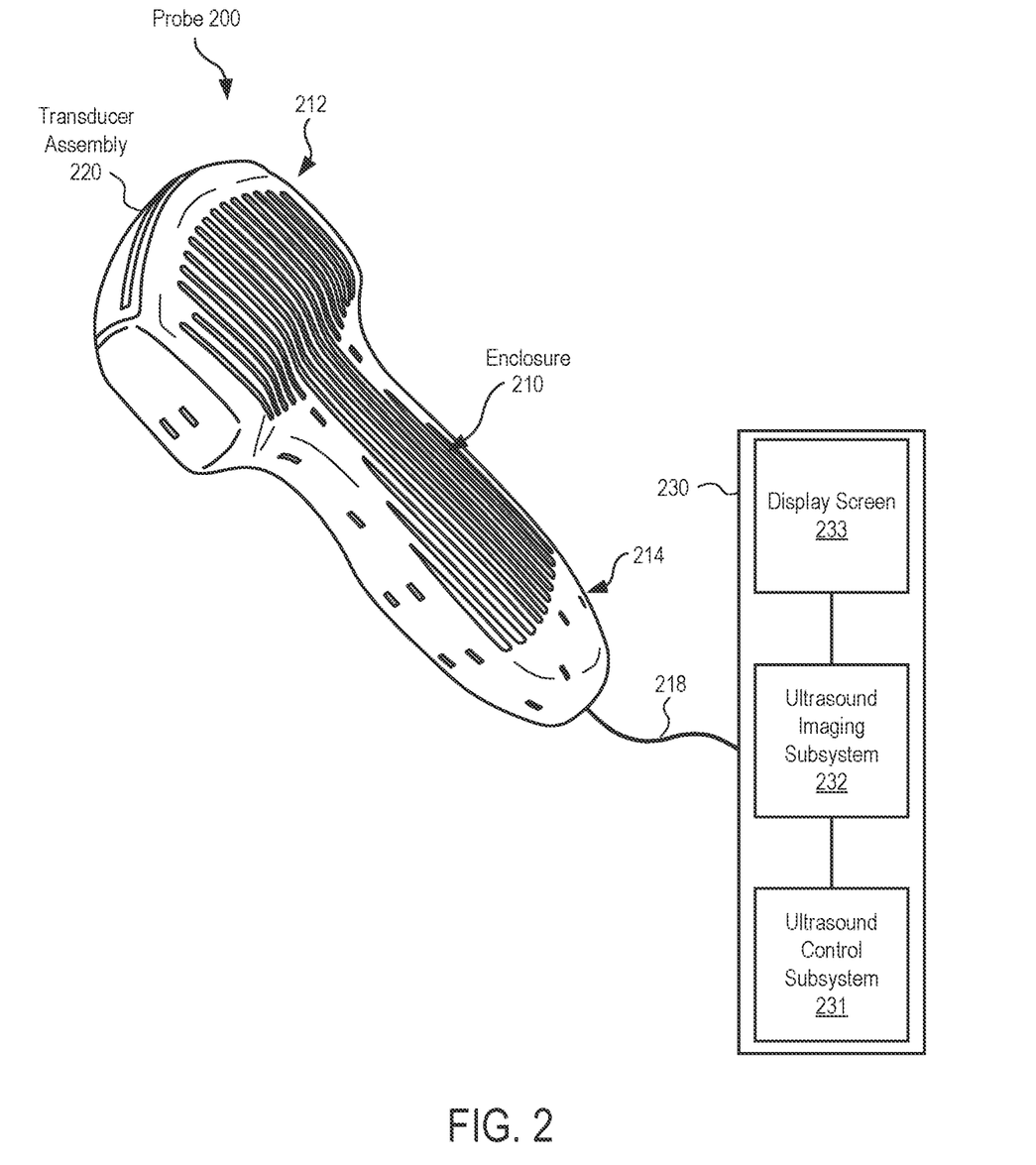
FIG. 2 illustrates one embodiment of an ultrasound transducer probe having an ultrasound transducer assembly.

FIG. 2 illustrates one embodiment of an ultrasound transducer probe having an ultrasound transducer assembly configured in accordance with an embodiment of the disclosed technology. Referring to FIG. 2, ultrasound transducer probe 200 includes an enclosure 210 extending between a distal end portion 212 and a proximal end portion 214. Enclosure 210 is configured to carry or house system electronics (e.g., one or more processors, integrated circuits, ASICs, FPGAs, beamformers, batteries and/or other power sources) disposed in an interior portion or cavity of enclosure 210. The system electronics (not shown) are electrically coupled to an ultrasound imaging system 230 via a cable 218 that is attached to the proximal end of the probe.

At the probe tip, a transducer assembly 220 having one or more transducer elements is electrically coupled to the system electronics. In operation, transducer assembly 220 transmits ultrasound energy from the one or more transducer elements toward a subject and receives ultrasound echoes from the subject. The ultrasound echoes are converted into electrical signals by transmit receive circuitry and electrically transmitted to the system electronics and to electronics (e.g., one or more processors, memory modules, beamformers, FPGAs, etc.) in ultrasound imaging system 230 configured to process the electrical signals and form one or more ultrasound images.

Capturing ultrasound data from a subject using an exemplary transducer assembly (e.g., the transducer assembly 220) generally includes generating ultrasound, transmitting ultrasound into the subject, and receiving ultrasound reflected by the subject. A wide range of frequencies of ultrasound may be used to capture ultrasound data, such as, for example, low frequency ultrasound (e.g., less than 15 MHz) and/or high frequency ultrasound (e.g., greater than or equal to 15 MHz) can be used. Those of ordinary skill in the art can readily determine which frequency range to use based on factors such as, for example, but not limited to, depth of imaging and/or desired resolution.

In one embodiment, ultrasound imaging system 230 includes ultrasound control subsystem 231 having one or more processors. At least one processor causes electrical currents to be sent to the transducer(s) of probe 200 to emit sound waves and also receives the electrical pulses from the probe that were created from the returning echoes. A processor processes the raw data associated with the received electrical pulses and forms an image that is sent to ultrasound imaging subsystem 232, which displays the image on display screen 233. Thus, display screen 233 displays ultrasound images from the ultrasound data processed by the processor of ultrasound control subsystem 231.

In one embodiment, the ultrasound system also has one or more user input devices (e.g., a keyboard, a cursor control device, etc.) that inputs data and allows the taking of measurements from the display of the ultrasound display subsystem, a disk storage device (e.g., hard, floppy, compact disks (CD), digital video discs (DVDs)) for storing the acquired images, and a printer that prints the image from the displayed data. These also have not been shown in FIG. 2 to avoid obscuring the techniques disclosed herein.

Figure 3:
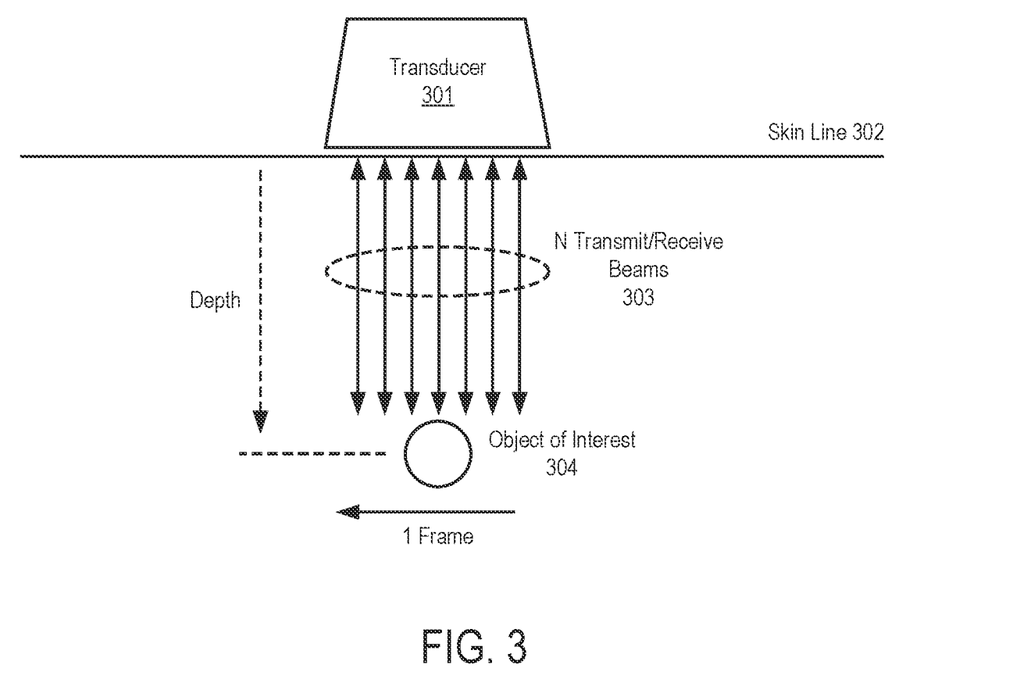
FIG. 3 illustrates a simplified description of frame acquisition for display performed by an ultrasound machine.

FIG. 3 illustrates a simplified description of frame acquisition for display performed by an ultrasound machine. A frame represents the amount of data needed to form an image on a display. The successive acquisition and display of frames of data allows the ultrasound machine to show the motion of the object being observed.

Figure 4:
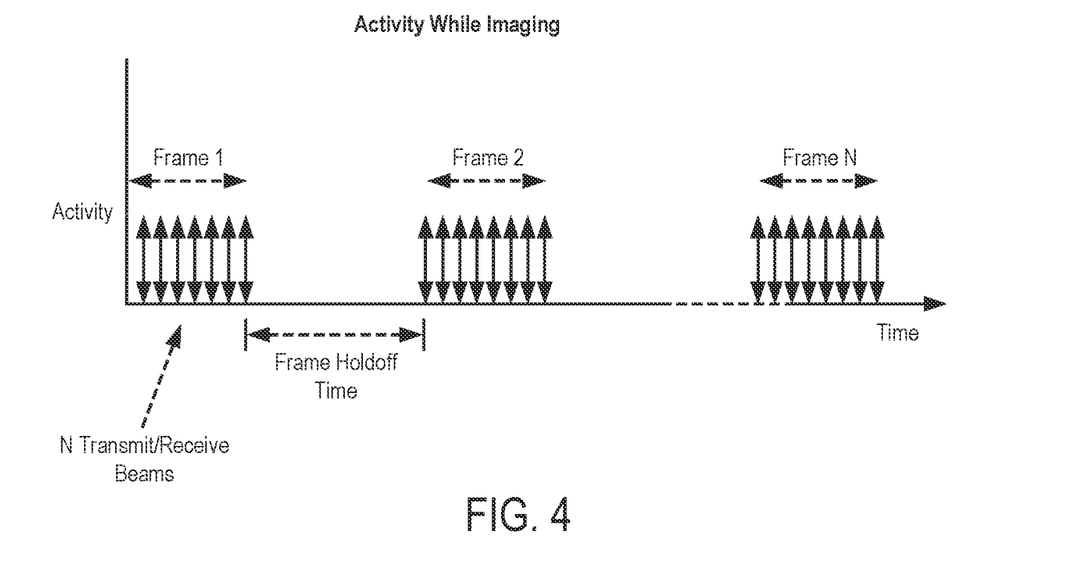
FIG. 4 illustrates the activity of one embodiment of an ultrasound machine while imaging.

Referring to FIG. 3, a frame consists of multiple (N) transmit beams 303 generated by transducer 301 toward an object of interest 304 that is located at a depth from skin line 302 and the echo returns from each of the transmit beams 303. In one embodiment, these beams 303 are closely spaced in time to minimize the time to produce a frame. The frame rate, which indicates how often the display is updated, is generally related to the acquisition time of the frame. For many applications, the ultrasound machine does not need to operate at a maximum frame rate either because the display electronics cannot keep up or because the user cannot perceive changes from one frame to the next. There is often a gap from the end of one frame to the start of the next which is referred to herein as the Frame Holdoff Time. FIG. 4 illustrates the activity of one embodiment of an ultrasound machine while imaging. Referring to FIG. 4, multiple transmit/receive beams are shown for Frames 1-N that are obtained over time. Between each of these frames is the Frame Holdoff Time.

Each of the N transmit/receive beams 303 in a frame can be further examined in terms of its activity. For the sake of simplicity, the receive path is discussed below in terms of dynamic power reduction; however, it should be understood that the dynamic power reduction techniques disclosed herein may be applied to the transmit path as well. In one embodiment, the transmit path refers to the electronics used to excite the individual transducer elements. Some common components of the transmit path are: a group of high voltage driver circuits used to energize the transducer elements, a set of delay circuits controlling the timing of signals to the high voltage drivers to control the focus of the generated acoustic beam and a waveform table (e.g., lookup table (LUT) or other memory) controlling the shape of the signal into the high voltage drivers. In one embodiment, the receive path comprises the electronics used to process the low level echoes detected by the transducer elements in response to the transmit beam. Typical operations performed by the electronics are: amplification of the return signals using both fixed and time variable amplifiers, filtering, signal conversion from the analog to the digital domain and receive beamforming. This last operation includes time variable digital gains to create a receive aperture with time alignment of the digitally sampled return signals to form a coherent receive beam.

Figure 5:
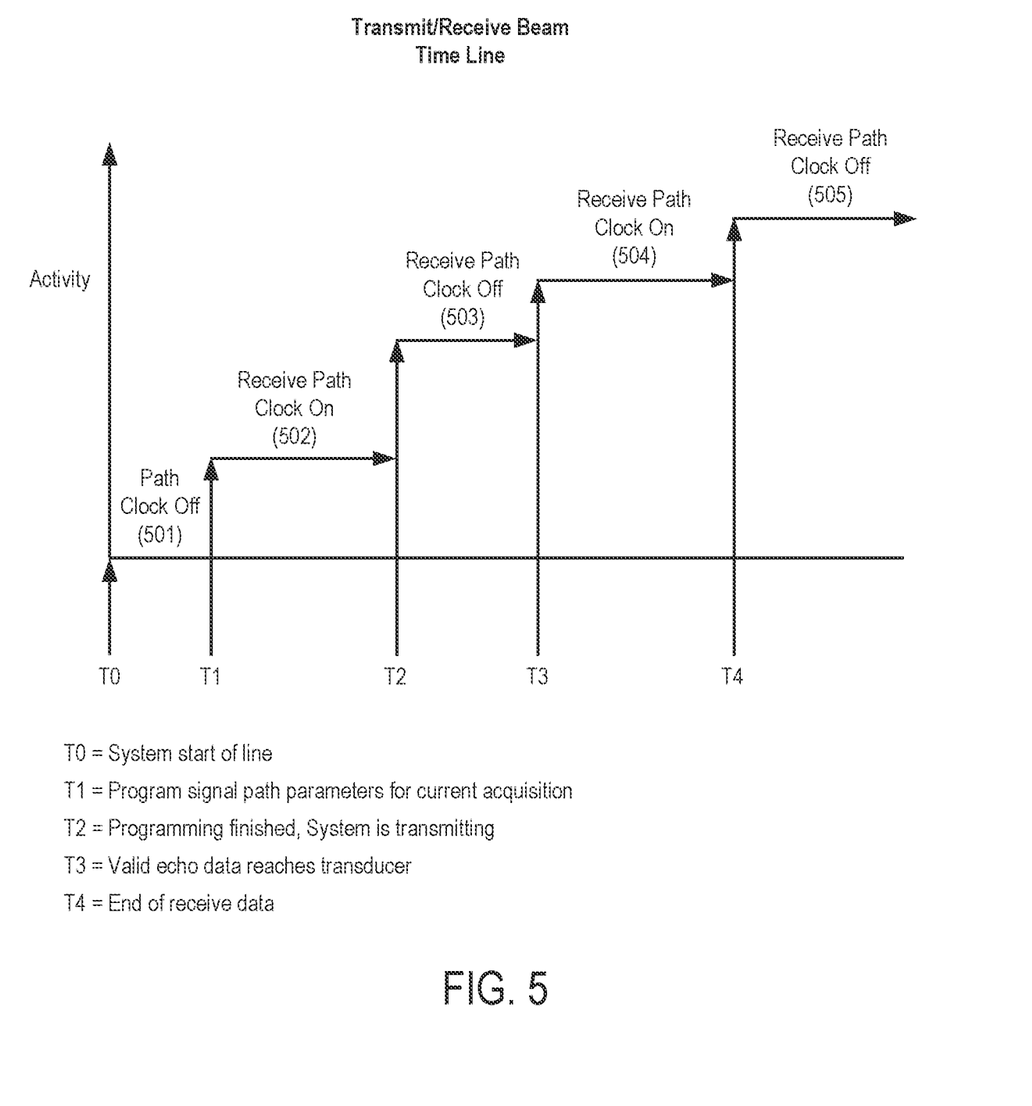
FIG. 5 illustrates basic actions of the clock(s) of a receive path of an ultrasound machine.

FIG. 5 illustrates basic actions of a receive path's clock(s) of one embodiment of an ultrasound machine. There are a number of events used to selectively turn the receive path clock on/off dynamically within the context of the timing for a single transmit/receive beam. This is a departure from the macro control described above as the clock is dynamically starting and stopping during imaging. In one embodiment, the decision to start and stop the clock is based on real-time signals during data acquisition.

Referring to FIG. 5, the receive path clock is off (501). The receive signal path has many parameters that are unique for each receive channel during a given transmit/receive operation. In one embodiment, the parameters are those discussed above with respect to the transmit and receive paths. In one embodiment, the parameters include individual transmit and receive delays for each transmitter and receiver, data to control time variable gains, and/or channel calibration data. In one embodiment, the clock to the receive path is active (502) in order to program the parameters (T1->T2 in FIG. 5). When programming has completed, the clock can be shut off (503) and remain off (T2->T3) until valid echo return data reaches the transducer at which point the clock remains on (504) for the duration of the data acquisition time (T3->T4). Finally, the clock shuts off (505) and remains off until it is time to re-program the receive path for the next acquisition.

Figure 6:
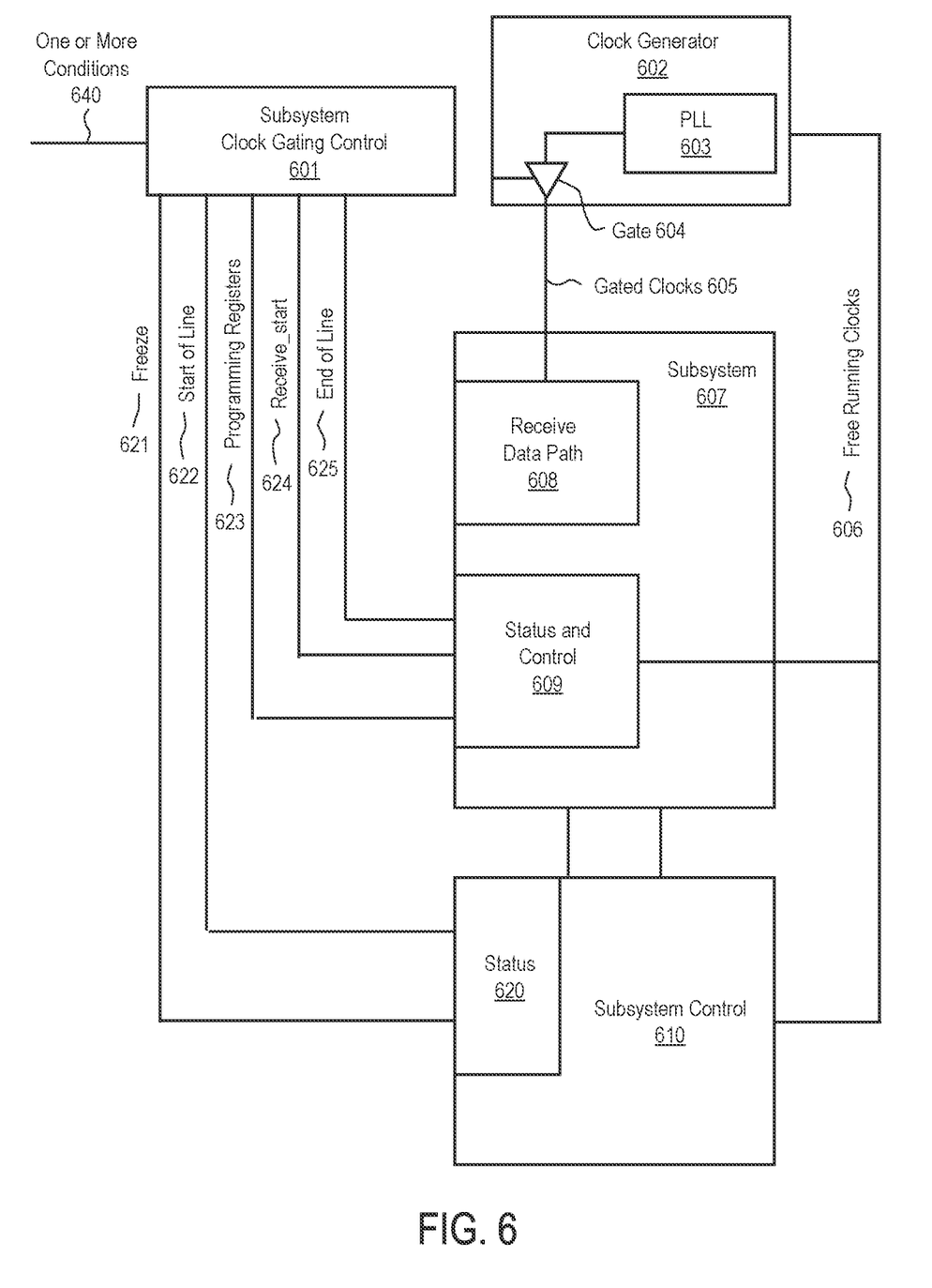
FIG. 6 is a block diagram of one embodiment of a portion of an ultrasound machine.

FIG. 6 is a block diagram of one embodiment of a portion of an ultrasound machine. Referring to FIG. 6, the ultrasound machine includes a clock gating control subsystem 601 coupled to a clock generator 602. In one embodiment, clock generator 602 includes a phased lock loop (PLL) 603 to generate clock signals. Clock generator 602 provides free running clocks 606 to subsystem 607 and ultrasound control subsystem 610. In one embodiment, subsystem 607 is part of the imaging subsystem and includes receive path 608 to receive and process acoustic signals (e.g., echoes) and a status and control module to provide state and control signals to clock gating control subsystem 601. In one embodiment, subsystem 607 includes the transmit path for the ultrasound machine to generate and transmit acoustic signals for the ultrasound machine.

Ultrasound control subsystem 610 controls operations of the ultrasound machine. In one embodiment, ultrasound control subsystem 610 generates status signals. In one embodiment, ultrasound control subsystem 610 generates status signals that are send to and received by clock gating control subsystem 601.

In one embodiment, the signals that are generated by subsystem 607 and ultrasound control subsystem 610 that are sent to and received by clock gating control subsystem 601 are real-time signals that comprise: a first signal indicating a user has indicated a desire to freeze the image currently being display on a display of the ultrasound system (e.g., freeze signal 621); a second signal indicating a start of a line (e.g., Start of Line signal 622); a third signal indicating registers are being programmed (the registers being for the receive path) (e.g., programming registers signal 623); a fourth signal indicating the receive path has been enabled to receive echoed acoustic signals (e.g., Receive_start signal 624); and a fifth signal indicating an end of the line has been reached (e.g., End of Line signal 625).

Clock gating control subsystem 601 uses signals 621-625 to perform clock control by gating/ungating clocks to different portions of the ultrasound machine. In one embodiment, clock gating control subsystem 601 uses signals 621-625 to perform clock control by gating/ungating clocks to different portions of the ultrasound machine according to the typical transmit/receive beam timeline during acquisition as shown in FIG. 5. For example, clock gating control subsystem 601 controls gate 604 to enable and disable one or more clocks 605 to receive path 608. For example, in response to freeze signal 621, clock gating control subsystem 601 controls gate 604 to disable one or more clocks 605 to receive path 608 as no echoes are going to be received while a user of the ultrasound machine freezes the display.

As another example, in response to programming registers signal 623, clock gating control subsystem 601 controls gate 604 to enable one or more clocks 605 to receive path 608 while registers are being programmed. After programming has been completed as indicated by a change in the programming registers signal 623, clock gating control subsystem 601 can control gate 604 to disable one or more clocks 605 to receive path 608 to place it in a reduced power consumption state until after the transmit section has finished transmitting beams and there are valid echoes returning to the transducer to be received by receive path 608.

As yet another example, in response to receive_start signal 624, clock gating control subsystem 601 controls gate 604 to enable one or more clocks 605 to receive path 608 to enable receive path 608 to be powered to receive valid echoes return to the transducer to be received and otherwise disable clocks 605 to receive path to place it in a reduced power consumption state. Similarly, clock gating control subsystem 601 uses receive_start signal 624 to disable one or more clocks 605 to the transmit path to place the transmit path in a reduced power consumption state while receive path 608 is receiving echoes (as the transmit path will not be transmitting beams during that time).

After finishing the receipt of echoes and an end of line has been reached as indicated by End of Line signal 625, clock gating control subsystem 601 can control gate 604 to disable one or more clocks 605 to receive path 608 to place it in a reduced power consumption state until a new line is going to be started and/or programming of registers is to occur.

As yet another example, in response to start of line signal 622, clock gating control subsystem 601 controls gate 604 to enable one or more clocks to the transmit path to enable the transmit path to be powered to transmit beams from the transducer. In one embodiment, a similar clock gating approach is applied to the transmit path in an effort to reduce power (i.e., to shut down the transmit logic when not transmitting).

In one embodiment, clock gating control subsystem 601 uses signals 621-625 along with one or more conditions (e.g., conditions 640) to perform clock control by gating/ungating clocks to different portions of the ultrasound machine. In this case, the clock control that is performed for certain sequences differs from that of the transmit/receive beam timeline during image acquisition shown in FIG. 5. Thus, clock gating control subsystem 601 handles other control sequences when performing clock control by gating/ungating clocks to different portions of the ultrasound machine.

In one embodiment, these sequences include one or more of the following:

1) imaging modes where register reprogramming is not needed between successive transmit/receive beams, and thus the time interval T1→T2 is 0. This is the case, for example, when reshooting of a line into an object to obtain a series of data for use in measuring changes in motion in the object on the line; if reshooting the line, the clock(s) does not need to be turned on during the time when the registers are normally being programmed; thus, the clock stays off until it is time to capture the returning echo values.

2) dummy ping generation where no data is acquired by receive path 608 but a time delay between transmit/receive beams is desired. In this case, there is no need to program registers during a "dummy" ping generation because transmit and receive are not going to occur. Thus, the clock(s) that are normally turned on when programming the registers can remain off; and 3) system initialization or a mode change where no data is acquired by receive path but register programming is necessary.

In the case of imaging modes where register reprogramming is not needed between successive transmit/receive beams, clock gating control subsystem 601 maintains the receive path in a reduced power state from T0 to T3 of FIG. 5. This behavior is identified by one of the input conditions 640. The condition represents a deviation from the baseline behavior in which the clock is enabled in response to 623.

In one embodiment, in the case of dummy ping generation, clock gating control subsystem 601 controls, using clock gating controller subsystem 601, the clocks to the receive path in response to a one of conditions 640 indicating whether or not the transducer is in ping generation mode. In such a case, since no data is to be acquired but a time delay between the transmit/receive beams is desired, if the ultrasound machine is in a ping generation mode, clock gating controller subsystem 601 maintains the clock signals to the receive path in a reduced power mode via clock gating when the receive_start signal 624 indicates that receive path 608 is to receive echoes.

In one embodiment, in the case of system initialization or a mode change mode changes refers to imaging modes and when the type of data being displayed changes. An example of this might be to switch from a gray scale image to a color image in this case the imaging stops and the system is re-initialized to acquire color data, clock gating control subsystem 601 controls, using clock gating controller subsystem 601, the clocks to the receive path in response to a one of conditions 640 indicating whether the ultrasound machine is in system initialization or a mode change. In such a case, clock gating control subsystem 601 enables clocks to the receive path when programming the registers but then does not re-enable the clocks to the receive path according to the time that echoes are to be returned to the transducer according to the time line in FIG. 5 as no data acquisition is to take place.

Figure 7:
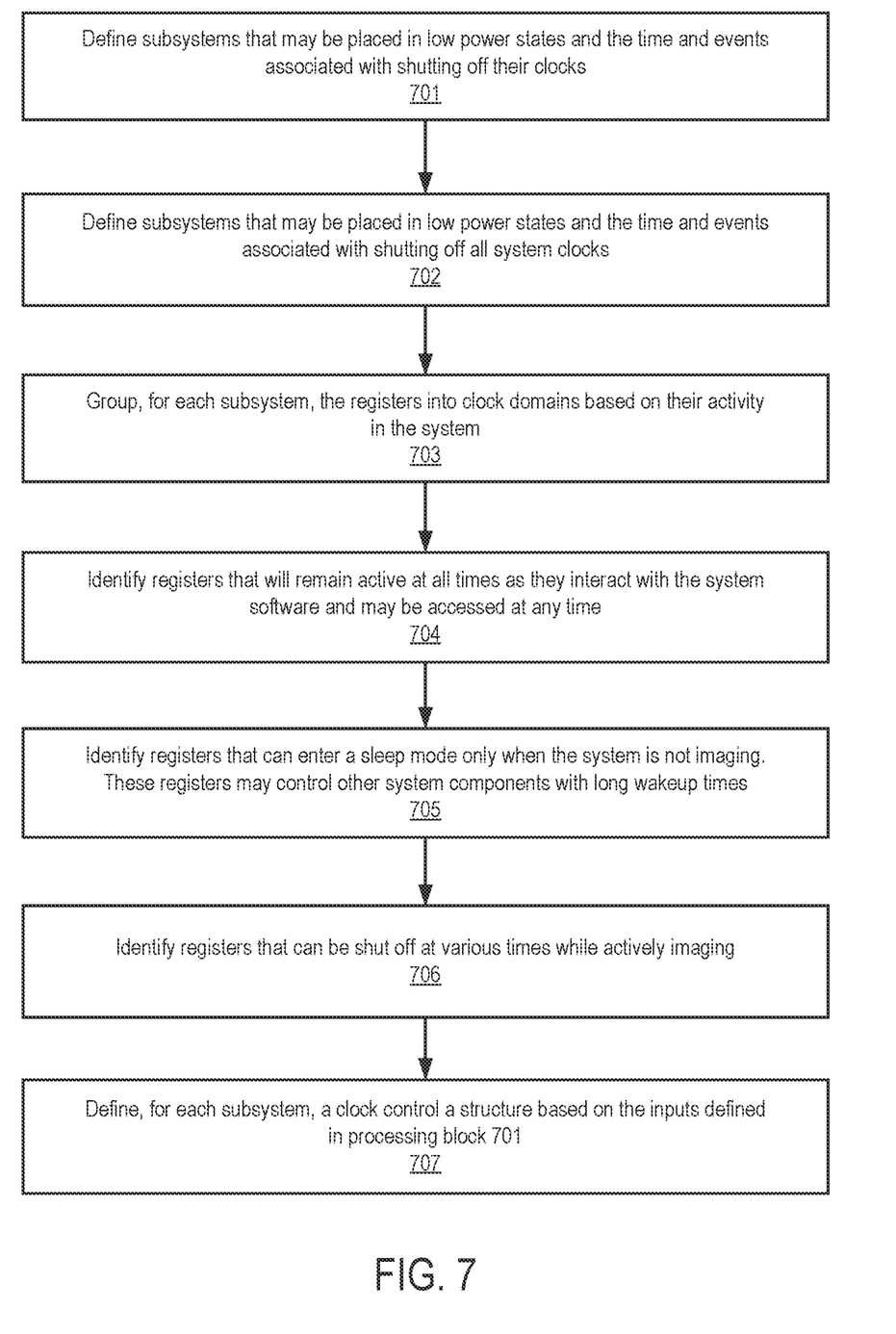
FIG. 7 is a flow diagram of one embodiment of a process for setting up dynamic power reduction for an ultrasound machine.

FIG. 7 is a flow diagram of one embodiment of a process to set up a dynamic power reduction process. The process is performed by processing logic that comprises hardware (circuitry, dedicated logic, etc.), software (e.g., software running on a chip), firmware, or a combination of the three.

Referring to FIG. 7, the process begins by defining subsystems that may be placed in low power states and the time and events associated with shutting off their clocks (processing block 701) and all system clocks (processing block 702). In one embodiment, dynamically gated clocks are treated as independent clocks derived from free running clocks at the same frequency. More specifically, in one embodiment, for each clock, processing logic examines all blocks attached to it and identifies which of these blocks contains logic that can be turned off at some point during normal operation without changing the block's function. Then the events associated with stopping the clock are listed.

The process continues by grouping, for each subsystem, the registers into clock domains based on their activity in the system (processing block 703). After grouping, the process identifies registers that will remain active at all times as they interact with the system software and may be accessed at any time (processing block 704), identifies registers that can enter a sleep mode only when the system is not imaging. These registers may control other system components with long wakeup times (processing block 705), and identifies registers that can be shut off at various times while actively imaging (processing block 706). In one embodiment, these are registers are in subsystem's data path or data path control.

Lastly, the process defines, for each subsystem, a clock control a structure based on the inputs defined in processing block 701. In one embodiment, the control structure is clocked by a free running clock and generates the real-time controls for its corresponding clock gating circuit.

Figure 8:
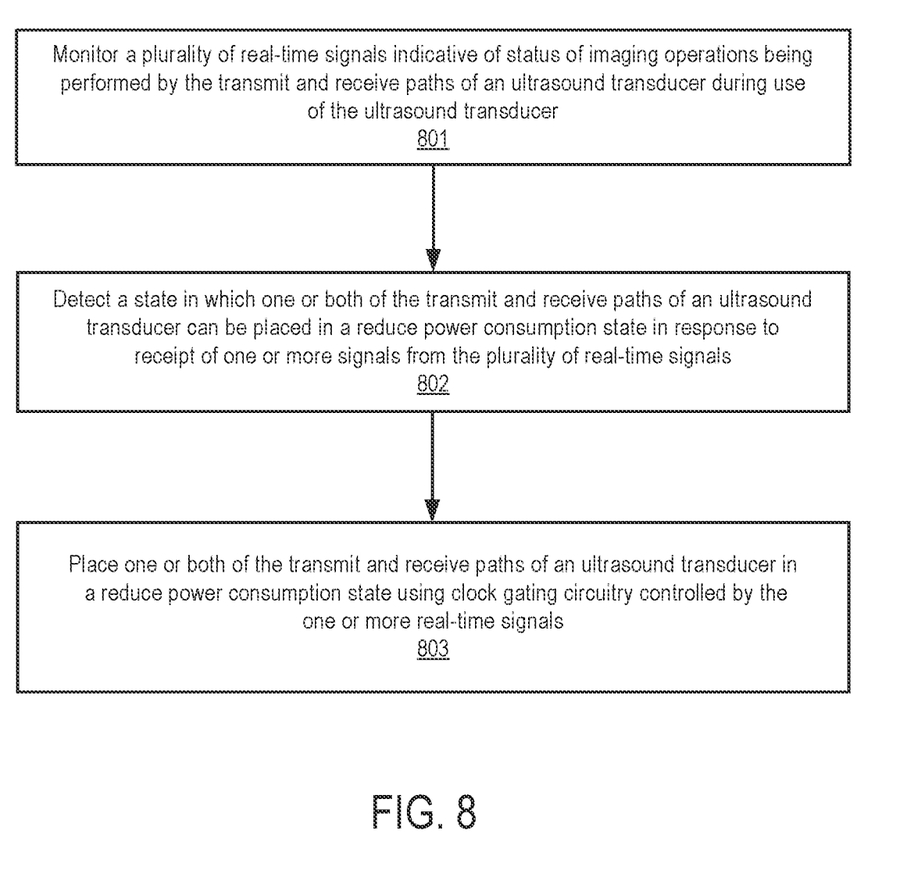
FIG. 8 is a flow diagram of one embodiment of a power reduction process for use by an ultrasound machine.

FIG. 8 is a flow diagram of one embodiment of a power reduction process for use by an ultrasound machine. The process is performed by processing logic that comprises hardware (circuitry, dedicated logic, etc.), software (e.g., software running on a chip), firmware, or a combination of the three.

Referring to FIG. 8, the process begins with processing logic monitoring a plurality of real-time signals indicative of status of imaging operations being performed by the transmit and receive paths of an ultrasound transducer during use of the ultrasound transducer (processing block 801).

While monitoring the real-time signals, processing logic automatic detects a state in which one or both of the transmit and receive paths of an ultrasound transducer can be placed in a reduce power consumption state in response to receipt of one or more signals from the plurality of real-time signals (processing block 802).

In response to detecting the state, processing logic places one or both of the transmit and receive paths of an ultrasound transducer in a reduce power consumption state using clock gating circuitry controlled by the one or more real-time signals (processing block 803).

In one embodiment, placing one or both of the transmit and receive paths of an ultrasound transducer in a reduce power consumption state comprises controlling, using a clock gating controller, the clock gating circuitry, in response to the one or more of the plurality of real-time signals, to gate a clock to the transmit path to turn off a transmitter of the transmit path after transmitting an acoustic signal for a line and controlling the clock gating circuitry to pass a previously gated second clock signal to the receive path to turn on a receiver when valid echo signals are expected to arrive at the receiver.

In one embodiment, placing one or both of the transmit and receive paths of an ultrasound transducer in a reduce power consumption state comprises controlling, using a clock gating controller, the clock gating circuitry, in response to the one or more of the real-time signals, to gate clocks to the transmit and receive paths at an end of one frame until another frame is started.

In one embodiment, placing one or both of the transmit and receive paths of an ultrasound transducer in a reduce power consumption state comprises controlling, using a clock gating controller, the clock gating circuitry, responsive to a first condition to ignore a first signal of the plurality of real-time signals indicating one or more receive path registers are being programmed, when the imaging mode indicates that reprogramming of the one or more receive path registers for transmit and receive operations for successive beams is not needed. In one embodiment, placing one or both of the transmit and receive paths of an ultrasound transducer in a reduce power consumption state comprises controlling, using a clock gating controller, the clock gating circuitry, responsive to the first condition, by passing clock signals to the receive path when programming the one or more receive path registers and thereafter not gate the clock signals to the receive path after programming the one or more receive path registers while waiting for valid echo signals return to the transducer if the transducer is in the imaging mode in which reprogramming of the one or more receive path registers for transmit and receive operations for successive beams is not needed. In one embodiment, the imaging mode includes reshooting of a line into an object to obtain a series of data for use in measuring changes in motion in the object on the line.

In one embodiment, placing one or both of the transmit and receive paths of an ultrasound transducer in a reduce power consumption state comprises controlling, using a clock gating controller, the clock gating circuitry, responsive to a first condition, by ignoring a first signal of the plurality of real-time signals indicating a start of the receive operation and maintaining gating of the clocks to the receive path after transmit beams have been transmitted from the transducer, the first condition indicating the transducer is in in ping generation mode.

In one embodiment, placing one or both of the transmit and receive paths of an ultrasound transducer in a reduce power consumption state comprises controlling, using a clock gating controller, the clock gating circuitry, responsive to a first condition, by ignoring a first signal of the plurality of real-time signals indicating a start of the receive operation and maintain gating of the clocks to the receive path after register programming, the first condition indicating the transducer is in a mode in which one or more receive path registers are program yet no valid echo signal acquisition is to occur. In one embodiment, the mode relates to system initialization or a mode change.

In one embodiment, placing one or both of the transmit and receive paths of an ultrasound transducer in a reduce power consumption state using clock gating circuitry controlled by the one or more real-time signals comprises controlling the circuits to gate or pass clock signals without intervention of system software.

In one embodiment, the process further comprises controlling, using the clock gating controller, the circuits to pass clock signals to the receive path when programming the one or more receive path registers and thereafter not gate the clock signals to the receive path after programming the one or more receive path registers while waiting for valid echo signals return to the transducer if the transducer is in the imaging mode in which reprogramming of the one or more receive path registers for transmit and receive operations for successive beams is not needed. In one embodiment, the imaging mode includes reshooting of a line into an object to obtain a series of data for use in measuring changes in motion in the object on the line.

In one embodiment, the plurality of real-time signals comprise: a first signal indicating a user has indicated a desire to freeze the image currently being display on a display of the ultrasound system (e.g., freeze signal 621); a second signal indicating a start of a line (e.g., Start of Line signal 622); a third signal indicating registers are being programmed (the registers being for the receive path) (e.g., programming registers signal 623); a fourth signal indicating the receive path has been enabled to receive echoed acoustic signals (e.g., Receive_start signal 624); and a fifth signal indicating an end of the line has been reached (e.g., End of Line signal 625).

As discussed above, power reduction reduces component temperatures for increased reliability, eases the demands on the system power supplies which reduces cost and increases battery life, eliminates/reduces the need for active cooling systems which reduces cost, noise and complexity, simplifies software control, enables the design of smaller form factor products, and allows for the integration of additional electronics into sealed components such as the transducer handle.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

A machine-readable medium includes any mechanism for storing or transmitting information in a form readable by a machine (e.g., a computer). For example, a machine-readable medium includes read only memory ("ROM"); random access memory ("RAM"); magnetic disk storage media; optical storage media; flash memory devices; etc.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims which in themselves recite only those features regarded as essential to the invention.

We claim:

1. An ultrasound system comprising:
a transducer assembly and imaging subsystem having a transmit data path having a transmitter to transmit acoustic signals and a receive data path having signal acquisition circuitry with a receiver to receive acoustic signals representing echoes;
a plurality of real-time signals indicative of status of imaging operations being performed by the transmit and receive paths; and
a control subsystem coupled to receive the plurality of real-time signals and to control clocking of one or more of the transmit and receive paths automatically via hardware in response to receipt of a plurality of real-time signals during a plurality of sequences, the control subsystem to provide one or more clocks to the transmit path to turn on a transmitter of the transmit path during a time interval while transmitting an acoustic signal and to provide one or more clocks the receive path to turn on a receiver while valid echo signals are expected to arrive at the receiver,
the control subsystem determining whether to provide one or more clocks to the receive path for programing receive path parameters during an imaging mode based on a state at least one of the plurality of real-time signals.

2. The ultrasound system of claim 1 wherein the state of the at least one of the plurality of real-time signals being in a first state signals to the control subsystem that reprogramming of the receive path parameters is not needed for one imaging mode to cause the control subsystem to gate clocks to the receive path during a time interval when reprograming of the receive path parameters is set to occur.

3. The ultrasound system of claim 2 wherein the one imaging mode includes when the transducer assembly is performing successive transmit and receive beams.

4. The ultrasound system defined in claim 2 wherein the control subsystem comprises:
clock gating circuitry coupled to the transmit and receive paths and having circuits to gate clocks to at least one of the transmit and receive paths; and
a clock gating controller coupled to the clock gating circuitry to control the circuits to gate or pass clock signals to at least one of the transmit and receive paths.

5. The ultrasound system defined in claim 4 wherein the clock gating controller is configured to control the clock gating circuitry, in response to the one or more signals, to gate a clock to the transmit path to turn off a transmitter of the transmit path after transmitting an acoustic signal for a line and to control the clock gating circuitry to pass a previously gated clock signal to the receive path to turn on a receiver when valid echo signals are expected to arrive at the receiver.

6. The ultrasound system defined in claim 4 wherein the clock gating controller is responsive to a first condition to ignore a first signal of the plurality of real-time signals indicating one or more receive path registers are being programmed when the imaging mode indicates that reprogramming of the one or more receive path registers for transmit and receive operations for successive beams is not needed.

7. The ultrasound system defined in claim 6 wherein the clock gating controller is configured to control the circuits to pass clock signals to the receive path when programming the one or more receive path registers and thereafter not gate the clock signals to the receive path after programming the one or more receive path registers while waiting for valid echo signals return to the transducer if the transducer is in the imaging mode in which reprogramming of the one or more receive path registers for transmit and receive operations for successive beams is not needed.

8. The ultrasound system defined in claim 7 wherein the imaging mode includes reshooting of a line into an object to obtain a series of data for use in measuring changes in motion in the object on the line.

9. The ultrasound system defined in claim 1 wherein the clock gating controller is configured to control the circuits to gate or pass clock signals without intervention of system software.

10. An ultrasound system comprising:
a transducer assembly and imaging subsystem having a transmit data path having a transmitter to transmit acoustic signals and a receive data path having signal acquisition circuitry with a receiver to receive acoustic signals representing echoes;
a plurality of real-time signals indicative of status of imaging operations being performed by the transmit and receive paths; and
a control subsystem coupled to receive the plurality of real-time signals and to control clocking of one or more of the transmit and receive paths automatically via hardware in response to receipt of a plurality of real-time signals during a plurality of sequences, the control subsystem to provide one or more clocks to the transmit path to turn on a transmitter of the transmit path during a time interval while transmitting an acoustic signal and to provide one or more clocks the receive path to turn on a receiver while valid echo signals are expected to arrive at the receiver,
the control subsystem determining whether to provide one or more clocks to the receive path during a mode based on a state at least one of the plurality of real-time signals indicative of whether the receive path is expected to acquire data.

11. The ultrasound system of claim 10 wherein the state of the at least one of the plurality of real-time signals being in a first state signals to the control subsystem that the receive path is not going to receive data in the mode to cause the control subsystem to gate clocks to the receive path during a time interval when in the mode.

12. The ultrasound system of claim 11 wherein the mode is a ping generation mode.

13. The ultrasound system defined in claim 12 and further wherein the control subsystem comprises:
clock gating circuitry coupled to the transmit and receive paths and having circuits to gate clocks to at least one of the transmit and receive paths; and
a clock gating controller coupled to the clock gating circuitry to control the circuits to gate or pass clock signals to at least one of the transmit and receive paths, and
further wherein the clock gating controller is configured to control the clock gating circuitry, in response to the one or more signals, to gate a clock to the transmit path to turn off a transmitter of the transmit path after transmitting an acoustic signal for a line and to control the clock gating circuitry to pass a previously gated clock signal to the receive path to turn on a receiver when valid echo signals are expected to arrive at the receiver.

14. The ultrasound system defined in claim 13 wherein the clock gating controller is responsive to a first condition to ignore a first signal of the plurality of real-time signals indicating a start of the receive operation and maintain gating of the clocks to the receive path after transmit beams have been transmitted from the transducer, the first condition indicating the transducer is in in ping generation mode.

15. The ultrasound system of claim 11 wherein the mode is a system initialization or change mode.

16. The ultrasound system defined in claim 15 and further wherein the control subsystem comprises:
   clock gating circuitry coupled to the transmit and receive paths and having circuits to gate clocks to at least one of the transmit and receive paths; and
   a clock gating controller coupled to the clock gating circuitry to control the circuits to gate or pass clock signals to at least one of the transmit and receive paths, and
   further wherein the clock gating controller is configured to control the clock gating circuitry, in response to the one or more signals, to gate a clock to the transmit path to turn off a transmitter of the transmit path after transmitting an acoustic signal for a line and to control the clock gating circuitry to pass a previously gated clock signal to the receive path to turn on a receiver when valid echo signals are expected to arrive at the receiver.

17. The ultrasound system defined in claim 16 wherein the clock gating controller is responsive to a first condition to ignore a first signal of the plurality of real-time signals indicating a start of the receive operation and maintain gating of the clocks to the receive path after register programming, the first condition indicating the transducer is in a mode in which one or more receive path registers are programed yet no valid echo signal acquisition is to occur.

18. A method comprising:
   monitoring a plurality of real-time signals indicative of status of imaging operations being performed by the transmit and receive paths of an ultrasound transducer during use of the ultrasound transducer;
   automatic detecting a state in which one or both of the transmit and receive paths of an ultrasound transducer can be placed in a reduced power consumption state in response to receipt of one or more signals from the plurality of real-time signals, wherein automatic detecting the state in which one or both of the transmit and receive paths of an ultrasound transducer can be placed in the reduced power consumption state comprises determining whether to provide one or more clocks to the receive path for programming receive path parameters during a mode based on a state at least one of the plurality of real-time signals; and
   placing one or both of the transmit and receive paths of an ultrasound transducer in a reduced power consumption state using clock gating circuitry controlled by the one or more real-time signals.

19. The method of claim 18 wherein a state of the at least one of the plurality of real-time signals being in a first state signals to the control subsystem that reprogramming of the receive path parameters is not needed for the mode to cause the control subsystem to gate clocks to the receive path during a time interval when reprograming of the receive path parameters is set to occur.

20. The method of claim 18 wherein the mode is a ping generation mode,
   a system initialization, or change mode.

* * * * *